United States Patent [19]

Takahashi et al.

[11] 4,250,117
[45] Feb. 10, 1981

[54] 4-HYDROXY-4-METHYL-CYCLOHEXEN-2-ONE-1

[75] Inventors: Katsuhiro Takahashi, Yokohama; Shigeru Muraki, Ryugasaki; Toshio Yoshida, Yokohama, all of Japan

[73] Assignee: Takasago Perfumery Co., Ltd., Tokyo, Japan

[21] Appl. No.: 932,076

[22] Filed: Aug. 8, 1978

[30] Foreign Application Priority Data

Aug. 8, 1977 [JP] Japan ................................. 52-94162

[51] Int. Cl.³ .......................................... C07C 49/713
[52] U.S. Cl. .................................. 568/377; 252/522 R
[58] Field of Search ..................................... 260/586 R

[56] References Cited

U.S. PATENT DOCUMENTS

| | | | |
|---|---|---|---|
| 3,957,887 | 5/1976 | Ichikawa et al. | 260/586 R |
| 4,010,205 | 3/1977 | Becker et al. | 260/586 R |
| 4,076,854 | 2/1978 | Light et al. | 260/586 R |
| 4,084,009 | 4/1978 | Light et al. | 260/586 R |

OTHER PUBLICATIONS

Gaoni, "Tetrahedron," vol. 28, pp. 5525–5531, (1972), Pergamon Press.

*Primary Examiner*—Norman Morgenstern
*Attorney, Agent, or Firm*—Sughrue, Rothwell, Mion, Zinn and Macpeak

[57] ABSTRACT

4-Hydroxy-4-methyl-cyclohexen-2-one-1 having the formula (I):

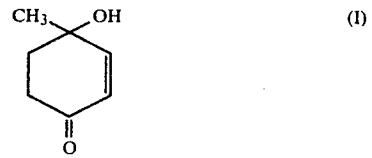

1 Claim, No Drawings

4-HYDROXY-4-METHYL-CYCLOHEXEN-2-ONE-1

BACKGROUND OF THE INVENTION

This invention relates to a novel compound useful as a perfume component. More specifically, this invention relates to 4-hydroxy-4-methyl-cyclohexan-2-one-1 useful as a perfume component.

SUMMARY OF THE INVENTION

This invention provides 4-hydroxy-4-methyl-cyclohexen-2-one-1 having the formula (I):

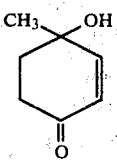

DETAILED DESCRIPTION OF THE INVENTION

4-Hydroxy-4-methyl-cyclohexen-2-one-1 having the formula (I) above [hereinafter "Compound (I)" of this invention] neat is a substance having a phenol-like or cattle pen-like odor. However, when Compound (I) is diluted to a great extent, it imparts a fragrance organoleptically felt to be warm and giving a sweet impression. It has been found that when Compound (I) is blended with other perfume components in a perfume composition in an amount of about 2 to about 15 ppm, preferably 5 to 10 ppm, favorable results which one can readily organoleptically recognize are obtained. For example, when Compound (I) of this invention is mixed with various synthetic essential oils such as petigrain oil, lavandine oil, lavender oil, orange oil, lemon oil, bergamot oil, peppermint oil, spearmint oil, etc., the naturalness of the odor of the blend can be markedly increased. Further, when Compound (I) is blended with other perfume components for perfumes, soaps, foods and the like, it can also impart a fragrance organoleptically felt to be warm and giving a sweet impression.

Compound (I) of this invention can be, for example, prepared in accordance with the following reaction schematic:

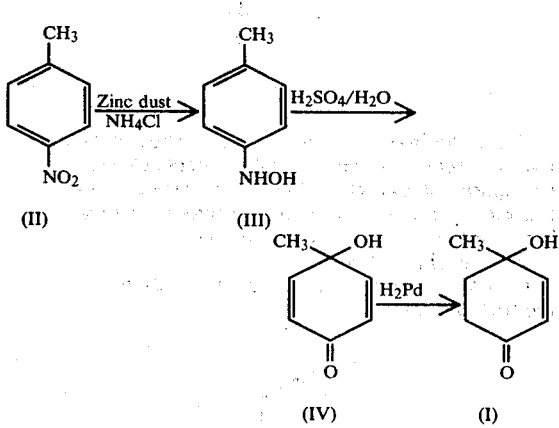

In the above-described reaction schematic, N-(p-methylphenyl)-hydroxylamine (III) can be obtained from p-nitrotoluene (II) using the nitrobenzene reduction method as described in, for example, H. Gilman, Organic Syntheses, Collective Vol. 1, 2nd Ed., pp 445–447 (1961), John Wiley & Sons, Inc., N.Y., or Y. Ogata et al, J. Am. Chem. Soc., 86, pp 3854–3858 (1964). More specifically, for example, 1 mole of p-nitrotoluene (II) is reduced with 2 moles of zinc dust in a solution of 1 mole of ammonium chloride, and the resulting product is recrystallized from a benzene-petroleum ether mixture to obtain Compound (III) having a melting point of 94° C. Subsequently, Compound (III) is treated with a 5% sulfuric acid aqueous solution while cooling to approximately 0° C., e.g., in accordance with the method described in S. Goodwin et al, J. Am. Chem. Soc., 79, pp 179–185 (1957). After extracting the resulting product with chloroform, the concentrate thus obtained is purified with a diethyl ether-benzene mixture on a silica gel chromatographic column to obtain pure p-toluquinol (IV) having a melting point of 76° to 78° C. Compound (IV) is then partially hydrogenated in ethyl alcohol with a 5% Pd/C catalyst at room temperature (e.g., about 20°–30° C.) under a hydrogen pressure of one atm. to obtain Compound (I) having a boiling point of 101.5° to 109.5° C./2 mmHg.

This invention is explained in more detail with reference to the following examples. Unless otherwise indicated herein, all parts, percents, ratios and the like are by weight.

The following Formulation Examples are given to illustrate representative examples of perfumes in which Compound (I) of this invention can be used. These Formulation Examples should not be construed as limiting the use of Compound (I) of this invention, however.

FORMULATION EXAMPLE 1

0.01 g (10 ppm) of Compound (I) of this invention was added to 1000 g of synthetic lavandine oil having the formulation shown in Table 1 below.

TABLE 1

| (Formulation of Synthetic Lavandine Oil) | |
|---|---|
| Components | Weight (g) |
| Cineole | 200 |
| Ocimene | 100 |
| Camphor | 90 |
| Aldehyde $C_{13}$ | 90 |
| (5,2,1,0)Tricyclo-3-decen-8-yl Acetate | 70 |
| Bornyl Acetate | 50 |
| iso-Pulegyl Acetate | 50 |
| Borneol | 42 |
| iso-Dihydro-lavandulyl Aldehyde | 42 |
| Octyl iso-Butyrate | 40 |
| Ethyl Amyl Ketone | 30 |
| Heptyl Aldehyde* | 28 |
| Hexyl Aldehyde* | 14 |
| Octyl Aldehyde* | 14 |
| Cuminaldehyde* | 14 |
| Linalyl iso-Valerate | 28 |
| Linalyl iso-Butyrate | 8 |
| Linalool Oxide | 8 |
| n-Octyl Alcohol | 14 |
| n-Hexyl Alcohol | 8 |
| n-Octyl Acetate | 8 |
| n-Hexyl Acetate | 14 |
| Dihydro Terpineol | 14 |
| Geraniol | 8 |
| n-Amyl Alcohol | 6 |
| Methyl Chrysanthemate | 10 |
| Total: | 1000 |

*1% in benzyl benzoate.

As a result of an organoleptic evaluation using 10 panelists, all of the 10 panelists recognized that the naturalness of the resulting perfume composition was markedly improved as compared with the same perfume composition to which Compound (I) of this invention was not added.

FORMULATION EXAMPLE 2

0.005 g (5 ppm) of Compound (I) of this invention was added to 1000 g of synthetic peppermint oil having the formulation shown in Table 2 below.

TABLE 2

(Formulation of Synthetic Peppermint Oil)

| Components | Weight (g) |
| --- | --- |
| Menthol | 474 |
| Menthone | 250 |
| 1,8-Cineole | 65 |
| Menthyl Acetate | 36 |
| iso-Menthone | 35 |
| Terpinene-4-ol | 32 |
| α-Terpineol | 20 |
| Menthofuran | 17 |
| l-Limonene | 15 |
| β-Pinene | 12 |
| α-Pinene | 9 |
| Piperitone | 5 |
| Caryophyllene | 5 |
| Linalool | 4 |
| 3-Octanol | 3 |
| p-Cymene | 3 |
| β-Myrcene | 3 |
| 1-Octen-3-ol | 2 |
| iso-Valeraldehyde | 2 |
| cis-Jasmone | 2 |
| iso-Amyl Alcohol | 0.6 |
| cis-3-Hexenol | 0.5 |
| Mint Lactone | 0.5 |
| 1-Octen-3-yl Isovalerate | 0.4 |
| n-Hexyl Aldehyde | 0.4 |
| t-2-Hexenol | 0.4 |
| Eugenol | 0.4 |
| n-Hexanol | 0.3 |
| t-Jasmone | 0.3 |
| 3-Octyl Acetate | 0.3 |
| 1-Octen-3-yl Acetate | 0.3 |
| Pulegone | 0.3 |
| iso-Valeric Acid | 0.3 |
| cis-3-Hexenyl Acetate | 0.2 |
| Citronellyl Acetate | 0.2 |
| Geranyl Acetone | 0.2 |
| Carbacrol | 0.2 |
| 2-Methylpropanol | 0.1 |
| Thymol | 0.1 |
| Total: | 1000 |

As a result of an organoleptic evaluation using 10 panelists, all of the 10 panelists recognized that the naturalness of the resulting perfume composition was markedly improved as compared with the same perfume composition to which Compound (I) of this invention was not added.

EXAMPLE

(i) Preparation of p-Tolylhydroxyl Amine 281 g (2.05 moles) of p-nitrotoluene, 125 g (2.35 moles) of ammonium chloride and 4 l of water were charged into a 10-l reaction flask. 310 g (4.74 moles) of zinc dust was added thereto at room temperature (i.e., about 20°–30° C.) over a period of 15 minutes while stirring the mixture, and the mixture was stirred for an additional 30 minutes. In this case, the temperature of the reaction system increased to 65° to 70° C. with stirring. Thereafter, the reaction mixture was filtered, and the filtrate was saturated with sodium chloride. The filtrate was allowed to stand in a cool place for 24 hours. The precipitated crystals were filtered, and recrystallized from 1 l of a benzene-petroleum ether (1:1 by volume) mixture to obtain 50 g of p-tolylhydroxyl amine.

(ii) Preparation of p-Toluquinol 50 g of p-tolylhydroxyl amine obtained in step (i) above was added incrementally to 1 l of a 5% sulfuric acid aqueous solution cooled to 0° C. using an ice-NaCl bath over a period of about 15 minutes while slowly stirring the mixture. After completion of the addition, the ice-NaCl bath was removed, and the mixture was slowly stirred at room temperature (i.e., about 20°–30° C.) for 12 hours. The reaction mixture was filtered, and the filtrate was extracted with 1 l of chloroform. The chloroform was distilled off from the extract to obtain 300 g of a concentrate. This concentrate was then chromatographed on a silica gel column, and eluted with a diethyl ether-benzene (1:1 by volume) mixture to obtain a fraction. The thus-obtained fraction was concentrated to obtain 15 g of p-toluquinol.

(iii) Preparation of 4-Hydroxy-4-methyl-cyclohexen-2-one-1

50 g of p-toluquinol obtained in step (ii) above was dissolved in 50 g of ethyl alcohol. The mixture was hydrogenated with 5% palladium-on-carbon as a catalyst while shaking the mixture at room temperature under a hydrogen pressure of one atm. When 80% of the amount of hydrogen theoretically necessary for hydrogenation to an extent of 0.5 mole was absorbed, the reaction was stopped. After filtering off the catalyst, the residue was distilled under reduced pressure to obtain 47 g of a fraction having a boiling point of 101.5°–109.5° C./2 mmHg. This fraction was a colorless liquid and had the following characteristics.

| | |
| --- | --- |
| Specific Gravity $d_{20}^{20}$: | 1.0842 |
| Refractive Index $n_D^{20}$: | 1.5163 |
| Mass Spectral Analysis: | $M^{\oplus}$ 126 111 (M—CH$_3$) |
| Infrared Analysis: | $\nu$ cm$^{-1}$ 3400 (—OH), 1675 (C=O) |
| Nuclear Magnetic Resonance Analysis: | |
| | δ ppm 1.4 (3H, s) H$_7$ |
| | 1.9–2.7 (4H, m) H$_5$, H$_6$ |
| | 3.3 (1H, m) OH |
| | 5.8 (1H, d) H$_3$ |
| | 6.7 (1H, d) H$_2$ |

The above results confirm that Compound (I) of this invention had the following formula:

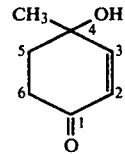

While the invention has been described in detail and with reference to specific embodiments thereof, it will be apparent to one skilled in the art that various changes and modifications can be made therein without departing from the spirit and scope thereof.

What is claimed is:

1. 4-Hydroxy-4-methyl-cyclohexen-2-one-1 having the formula (I):

* * * * *